(12) United States Patent
Huang et al.

(10) Patent No.: US 11,999,688 B2
(45) Date of Patent: Jun. 4, 2024

(54) METHOD FOR PRODUCING DICARBOXYLIC ACID

(71) Applicant: DALIAN INSTITUTE OF CHEMICAL PHYSICS, CHINESE ACADEMY OF SCIENCES, Dalian (CN)

(72) Inventors: Shengjun Huang, Dalian (CN); Dazhi Zhang, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 725 days.

(21) Appl. No.: 17/253,779

(22) PCT Filed: Jun. 28, 2018

(86) PCT No.: PCT/CN2018/093445
§ 371 (c)(1),
(2) Date: Dec. 18, 2020

(87) PCT Pub. No.: WO2019/242038
PCT Pub. Date: Dec. 26, 2019

(65) Prior Publication Data
US 2021/0147331 A1    May 20, 2021

(30) Foreign Application Priority Data

Jun. 20, 2018   (CN) .......................... 201810638022.9

(51) Int. Cl.
C07C 51/31    (2006.01)
B01J 21/08    (2006.01)
(Continued)

(52) U.S. Cl.
CPC ............. *C07C 51/316* (2013.01); *B01J 21/08* (2013.01); *B01J 23/22* (2013.01); *B01J 27/125* (2013.01);
(Continued)

(58) Field of Classification Search
CPC ....... C07C 51/316; C07C 51/31; C07C 67/04; C07C 67/297; C07C 67/347; B01J 27/25
See application file for complete search history.

(56) References Cited

U.S. PATENT DOCUMENTS 3,636,101 A * 1/1972 Doumani .............. C07C 51/316
                                                                  568/942
5,321,155 A    6/1994 Drinkard et al.
6,093,857 A    7/2000 Fischer et al.

FOREIGN PATENT DOCUMENTS

CN    1143948 A    2/1997
CN    102614920 A    8/2012
(Continued)

OTHER PUBLICATIONS

US 5,179,226 A, 01/1993, Inoue et al. (withdrawn)
(Continued)

*Primary Examiner* — Yate' K Cutliff
(74) *Attorney, Agent, or Firm* — Maier & Maier, PLLC

(57) ABSTRACT

A method for producing dicarboxylic acid. The method includes: subjecting a raw material system including a cyclic olefin and a lower monocarboxylic acid to an addition reaction in the presence of an addition reaction catalyst to generate an intermediate product system including cyclic carboxylic acid ester; and subjecting the intermediate product system including cyclic carboxylic acid ester to a ring-opening and oxidation reaction in the presence of an oxidant and an oxidation catalyst to generate a corresponding dicarboxylic acid product. The addition reaction in the dicarboxylic acid synthesis route achieves a high single-pass con-
(Continued)

version rate, and the selectivity of the corresponding cyclic carboxylic acid ester is high. The addition-oxidation synthesis route achieves faster reaction rates for both the addition reaction and oxidation reaction, and high yield of corresponding dicarboxylic acid product. The addition-oxidation based synthesis route is suitable for continuous, stable and large-scale production of corresponding dicarboxylic acid product.

12 Claims, 1 Drawing Sheet

(51) Int. Cl.
| | | |
|---|---|---|
| *B01J 23/22* | (2006.01) | |
| *B01J 27/125* | (2006.01) | |
| *B01J 27/188* | (2006.01) | |
| *B01J 27/19* | (2006.01) | |
| *B01J 27/25* | (2006.01) | |
| *B01J 29/08* | (2006.01) | |
| *B01J 29/40* | (2006.01) | |
| *B01J 31/08* | (2006.01) | |
| *C07C 67/04* | (2006.01) | |
| *C07C 67/347* | (2006.01) | |

(52) U.S. Cl.
CPC ............ *B01J 27/188* (2013.01); *B01J 27/19* (2013.01); *B01J 27/25* (2013.01); *B01J 29/084* (2013.01); *B01J 29/40* (2013.01); *B01J 31/08* (2013.01); *C07C 51/31* (2013.01); *C07C 67/04* (2013.01); *C07C 67/347* (2013.01)

(56) References Cited

FOREIGN PATENT DOCUMENTS

| | | | | |
|---|---|---|---|---|
| CN | 103787877 A | | 5/2014 | |
| CN | 106349019 A | | 1/2017 | |
| CN | 111253240 A | | 6/2020 | |
| GB | 1402480 | * | 8/1975 | ............. C07C 51/32 |
| GB | 1402480 A | | 8/1975 | |
| JP | 50-35108 A | | 4/1975 | |
| JP | H05155811 | * | 6/1993 | ............. C07B 61/00 |
| SU | 937444 A1 | | 6/1982 | |

OTHER PUBLICATIONS

JPH05155811, Inoue, K. et al., Production of Carboxylic Acid Cyclohexyl ester, English translation,10 pages (Year: 1993).*
Kumar et al., "Development of a Novel Catalytic Distillation Process for Cyclohexanol Production: Mini Plant Experiments and Complementary Process Simulations," Organic Process Research & Development, 2011; vol. 15, No. 3; pp. 527-539.
International Search Report dated Feb. 2019 in corresponding International application No. PCT/CN2018/093445; 4 pages.
Chinese Office Action dated Jun. 18, 2020 in corresponding International application No. 201810638022.9; 15 pages.
Chinese Search Report dated Jun. 8, 2020 in corresponding International application No. 201810638022.9; 8 pages.
Synthesis of AgWCNx Nanocomposites for One-Step Conversion of Cyclohexene to Adipic Acid and Its Mechanistic Studies, «Chemistry-A European Journal» , vol. 23., Reena Goyal, et al., pp. 16555-16565, Nov. 2, 2017.

* cited by examiner

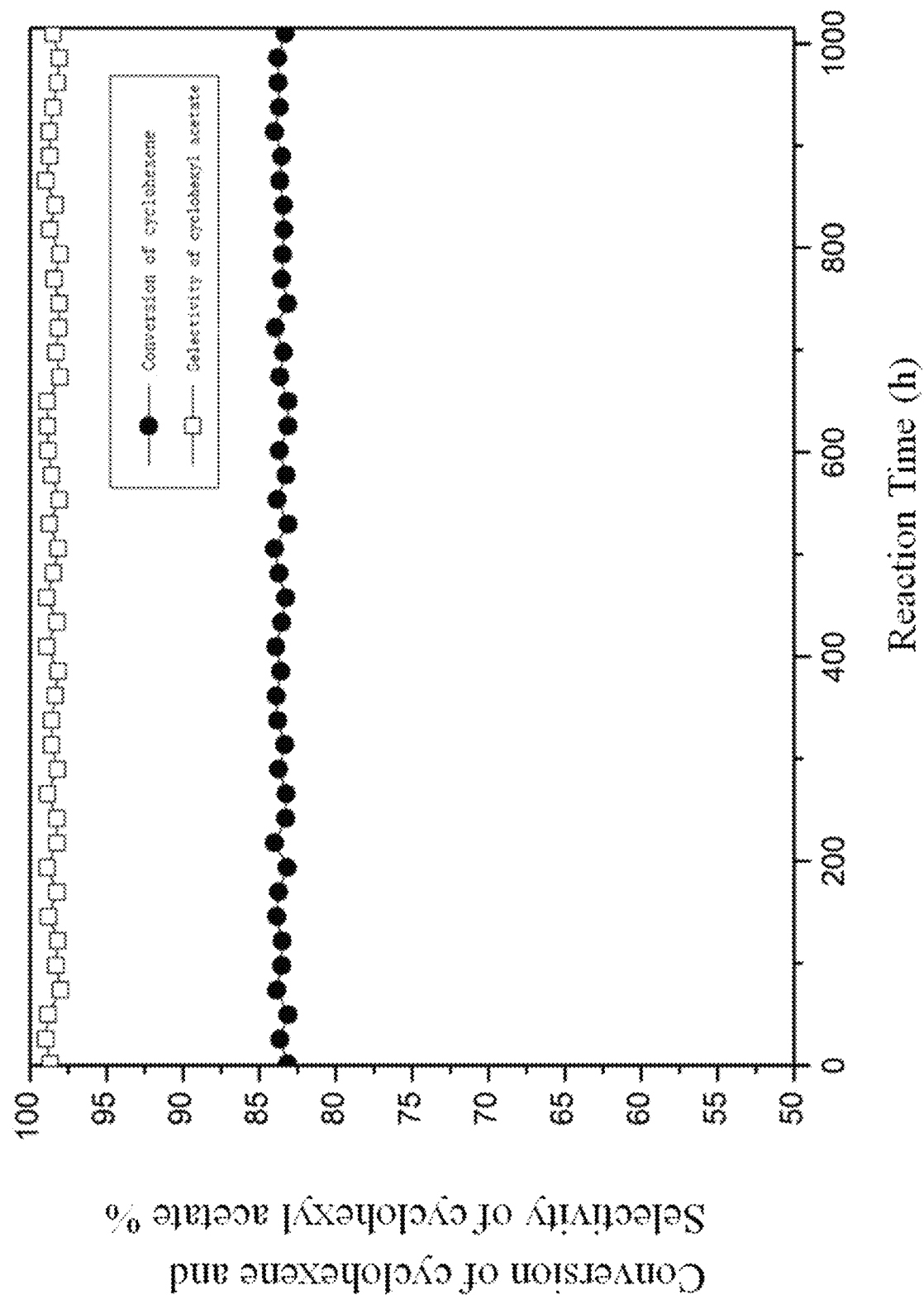

METHOD FOR PRODUCING DICARBOXYLIC ACID

TECHNICAL FIELD

The present application relates to a method for producing dicarboxylic acid, which belongs to the new technical field of chemical production and manufacturing.

BACKGROUND

Dicarboxylic acid is an important chemical precursor material in polymer chemical industry and organic synthesis. Adipic acid is a representative substance among dicarboxylic acids. At present, it is mainly produced through the oxidation of cyclohexanol/cyclohexanone. Representative production routes are as follows: 1) cyclohexane is oxidized to produce cyclohexanol-cyclohexanone (KA oil) which is then oxidized to produce adipic acid; 2) cyclohexene is hydrated to produce cyclohexanol which is then oxidized to produce adipic acid. In the first production route, the single-pass conversion rate of cyclohexane is low in the step of cyclohexane oxidation to KA oil, which is less than 6%, and the operating conditions of the reaction process are not easy to control which would easily incur accidents. In the second production route, the hydration of cyclohexene has significant advantages in operating safety of the reaction process. However, there are still the following problems: 1) High purity requirements for cyclohexene and water raw materials, the reason for which is that the solubilities of upstream materials such as cyclohexene and cyclohexane in water are close, and the content of cyclohexane impurity in the cyclohexene raw materials must be reduced as much as possible to reduce the negative impact of the dissolution effect of cyclohexane impurity on the reaction rate; and the oxygen content of the water in the materials has an impact on the hydration reaction and must be reduced as much as possible; 2) The hydration reaction rate is slow, the reason for which is that due to the difference in polarity, the solubility of cyclohexene in water is very small, and thus the reaction concentration limits the reaction rate; 3) the single-pass conversion rate is low, the reason for which is that: the hydration reaction of cyclohexene is a thermodynamic equilibrium restricted reaction, according to reports, even if the residence time of the cyclohexene raw material in the slurry reactor is extended, the single pass-conversion rate of the cyclohexene can only reach about 12%; 4) The reaction operation procedures, subsequent separation and recycling costs are relatively high, the reason for which is that: the reaction system is a three-phase complex system of "oil phase (cyclohexene)-water phase-solid phase (molecular sieve)", for which strong agitation is required to form an emulsified system to improve the mass transfer of the reaction, the corresponding abrasion and consumption of the catalyst would occur during the stirring process, and the fine catalyst produced by abrasion brings difficulties to subsequent material separation, and in addition, due to the low single-pass conversion rate of cyclohexene, a large amount of the un-reacted cyclohexene needs to be recycled.

In addition to the above-mentioned representative routes, other synthetic routes of adipic acid have also been disclosed. U.S. Pat. No. 5,166,421 disclosed a method for producing adipic acid by twice hydroformylation with butadiene as raw materials. The total yield of adipic acid by this route is not high, but the cost of the precious metal catalyst used is relatively high. GB1402480 disclosed a method of firstly carrying out an addition reaction between cyclic mono-olefin and saturated aliphatic dibasic acid containing from 4 to 12 carbon atoms to generate corresponding dibasic esters, and then oxidizing the resulted esters to produce dicarboxylic acids. Since the reaction raw materials used in the addition reaction are solid-liquid two-phase, such method can only be operated intermittently, and thus the reaction efficiency is not high, and the final product and the raw materials are not easy to separate. Therefore, based on the current state of the art, it is still necessary to develop a new method for producing dicarboxylic acid, which should possess the characteristics of safe operating conditions, fast reaction rate, high reaction conversion rate and high atom utilization.

SUMMARY

According to one aspect of the present application, a method for producing dicarboxylic acid is provided. The method comprises the following steps:

1) an intermediate product system comprising cyclic carboxylic acid ester is obtained from a raw material system comprising a cyclic olefin and a lower monocarboxylic acid by an addition reaction in the presence of an addition reaction catalyst;

2) a ring-opening oxidation reaction is carried out in the presence of an oxidant and an oxidation catalyst to produce a corresponding dicarboxylic acid product from the intermediate product system Preferably, the cyclic olefin comprises five or more carbon atoms and a carbon-carbon double bond structure.

The cyclic olefin is selected from the compound with the chemical formula represented by formula I, the compound with a chemical formula represented by formula II, the compound with the chemical formula represented by formula III, the compound with the chemical formula represented by formula IV, and any combination thereof:

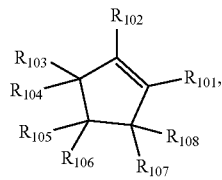

Formula I

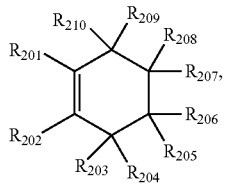

Formula II

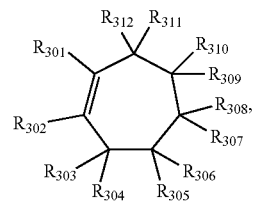

Formula III

Formula IV

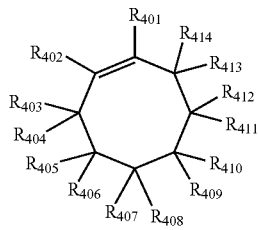

wherein, $R_{101}$, $R_{102}$, $R_{103}$, $R_{104}$, $R_{105}$, $R_{106}$, $R_{107}$, and $R_{108}$ in formula I are independently selected from H, $C_1$ to $C_3$ hydrocarbon group, halogen element or $C_1$ to $C_3$ halogenated hydrocarbon group. Preferably, any of $R_{101}$, $R_{102}$, $R_{103}$, $R_{104}$, $R_{105}$, $R_{106}$, $R_{107}$ and $R_{108}$ in formula I is $C_1$ to $C_3$ alkyl group.

$R_{201}$, $R_{202}$, $R_{203}$, $R_{204}$, $R_{205}$, $R_{206}$, $R_{207}$, $R_{208}$, $R_{209}$ and $R_{21}$ in formula II are independently selected from H, $C_1$ to $C_3$ hydrocarbon group, halogen element or $C_1$ to $C_3$ halogenated hydrocarbon group. Preferably, any of $R_{201}$, $R_{202}$, $R_{203}$, $R_{204}$, $R_{205}$, $R_{206}$, $R_{207}$, $R_{208}$, $R_{209}$ and $R_{210}$ in formula II is $C_1$ to $C_3$ alkyl group.

$R_{301}$, $R_{302}$, $R_{303}$, $R_{304}$, $R_{305}$, $R_{306}$, $R_{307}$, $R_{308}$, $R_{309}$, $R_{310}$, $R_{311}$ and $R_{312}$ in formula III are independently selected from H, $C_1$ to $C_3$ hydrocarbon group, halogen element or $C_1$ to $C_3$ halogenated hydrocarbon group. Preferably, any of $R_{301}$, $R_{302}$, $R_{303}$, $R_{304}$, $R_{305}$, $R_{306}$, $R_{307}$, $R_{308}$, $R_{309}$, $R_{310}$, $R_{311}$ and $R_{312}$ in formula III is $C_1$ to $C_3$ alkyl group.

$R_{401}$, $R_{402}$, $R_{403}$, $R_{404}$, $R_{405}$, $R_{406}$, $R_{407}$, $R_{408}$, $R_{409}$, $R_{410}$, $R_{411}$, $R_{412}$, $R_{413}$, and $R_{414}$ in formula IV are independently selected from H, $C_1$ to $C_3$ hydrocarbon group, halogen element or $C_1$ to $C_3$ halogenated hydrocarbon group. Preferably, any of $R_{401}$, $R_{402}$, $R_{403}$, $R_{404}$, $R_{405}$, $R_{406}$, $R_{407}$, $R_{408}$, $R_{409}$, $R_{410}$, $R_{411}$, $R_{412}$, $R_{413}$, and $R_{414}$ in formula IV is $C_1$ to $C_3$ alkyl group.

Preferably, the lower monocarboxylic acid is selected from at least one compound with a chemical formula represented by formula V:

Formula V

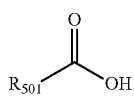

wherein, $R_{501}$ is selected from H, $C_1$ to $C_3$ hydrocarbon group or $C_1$ to $C_3$ halogenated hydrocarbon group. Preferably, $R_{501}$ is selected from $C_1$ to $C_3$ alkyl groups or vinyl. More preferably, the lower monocarboxylic acid is selected from acetic acid, formic acid, and trifluoroacetic acid and any combination thereof.

Correspondingly, the products of the addition reaction are shown in the following formula VI, formula VII, formula VIII, and formula IX:

Formula VI

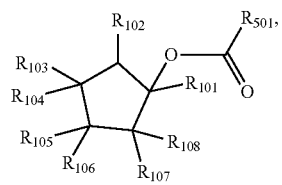

Formula VII

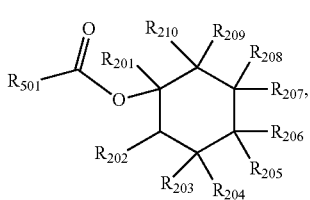

Formula VIII

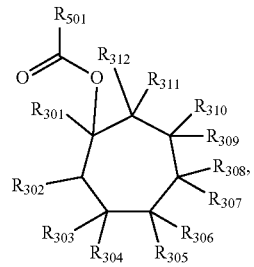

Formula IX

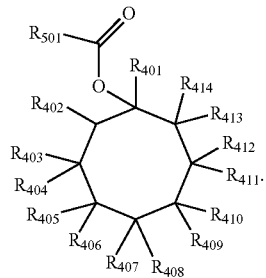

In addition, the products of the ring-opening oxidation reaction are shown in the following formulas X, XI, XII and XIII.

Formula X

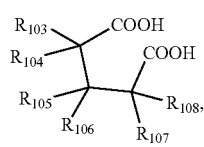

Formula XI

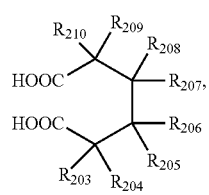

Formula XII

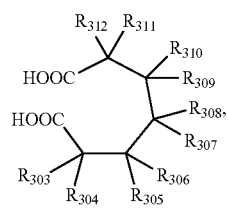

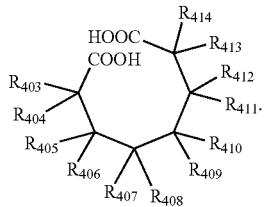

Formula XIII

Compared with the dibasic acid used, the lower monocarboxylic acid, especially acetic acid, has better mutual solubility with the cyclic olefin. The contact between the reactants is thus better, and the ratio of reactants can be adjusted in a wider range, which can have higher reactivity and selectivity. In addition, the reaction mixture of acetic acid and cyclic olefin is liquid phase, and thus the reaction in the present invention can be continuously operated using a fixed bed, which has higher efficiency.

The intermediate product (such as cyclohexyl acetate) of the addition reaction obtained by using the saturated monocarboxylic acid of the present invention as raw material is liquid. The use of liquid cyclohexyl acetate is more advantageous to the subsequent oxidation operation, the oxidation reaction step can be operated continuously, and the reaction speed is faster and the selectivity is higher. The dicarboxylic acid product obtained after the oxidation reaction of the present invention is easier to be separated from the saturated monocarboxylic acid. The saturated monocarboxylic acid used in the present invention is cheaper.

Preferably, the addition reaction catalyst in step 1) comprises at least one of a supported inorganic acid, a cation exchange resin and a molecular sieve.

Preferably, the acid catalyst is solid acid catalyst.

The solid acid catalyst has the following advantages:
a) higher conversion rate and selectivity can be achieved;
b) a fixed bed can be used for continuous operation;
c) product and catalyst can be easily separated; and
d) Less corrosiveness to equipment can be achieved.

Preferably, the supported inorganic acid catalyst contains an inorganic acid and a support; the inorganic acid is selected from sodium hydrogen sulfate, sodium hydrogen phosphate, $AlCl_3$, heteropoly acid and any combination thereof, and the support is selected from silica, diatomite, kaolin and any combination thereof, wherein the weight percentage of the inorganic acid in the supported inorganic acid ranges from 5% to 25%.

Preferably, the cation exchange resin is a sulfonic acid type-macroporous strong acid ion exchange resin whose Hammett index of acid strength is $H_0 < -10$, and the $H^+$ exchange capacity of the ion exchange resin is greater than 1.0 mmol/L; The molecular sieve is selected from HY, Hβ and HZSM-5 molecular sieves with topological structures of FAU, BEA, and MFI, and any combination thereof; and as measured by $NH_3$ chemisorption determination, the molecular sieve has a weak acid site density ranging from 0.005 mmol/g to 0.35 mmol/g, a medium-strength acid site density ranging from 0.01 mmol/g to 0.5 mmol/g, and a strong acid site density ranging from 0.003 mmol/g to 0.15 mmol/g.

Preferably, the molar ratio of the lower monocarboxylic acid to the cyclic olefin is in a range from 0.2 to 10.0, and the space velocity of the cyclic olefin is in a range from 0.6 to 3.0 g·g$^{-1}$·h$^{-1}$.

In the addition reaction, the molar ratio of the lower monocarboxylic acid to the cyclic olefin can be any value of 0.2, 1, 2, 3, 4, 5, 6, 7, 8, 9, 10 or any value in the range determined by any two of 0.2, 1, 2, 3, 4, 5, 6, 7, 8, 9 and 10. The space velocity of the cyclic olefin can be 0.6 g·g$^{-1}$·h$^{-1}$, 1 g·g$^{-1}$·h$^{-1}$, 1.5 g·g$^{-1}$·h$^{-1}$, 2.0 g·g$^{-1}$·h$^{-1}$, 2.5 g·g$^{-1}$·h$^{-1}$, 3.0 g·g$^{-1}$·h$^{-1}$ or any value in the range determined by any two of 0.6 g·g$^{-1}$·h$^{-1}$, 1 g·g$^{-1}$·h$^{-1}$, 1.5 g·g$^{-1}$·h$^{-1}$, 2.0 g·g$^{-1}$·h$^{-1}$, 2.5 g·g$^{-1}$·h$^{-1}$, 3.0 g·g$^{-1}$·h$^{-1}$.

Preferably, the addition reaction is carried out in one or more reactors, and the reactor is selected from a fixed bed reactor, a kettle-type reactor and combination thereof.

Preferably, the addition reaction is carried out under a pressure ranging from 0.1 to 2.0 MPa, and a reaction temperature ranging from 50 to 150° C.

The pressure for carrying out the addition reaction may be any value of 0.1 MPa, 0.5 MPa, 1.0 MPa, 1.5 MPa, 2.0 MPa or any value in the range determined by any two of 0.1 MPa, 0.5 MPa, 1.0 MPa, 1.5 MPa, and 2.0 MPa.

The lower limit of the temperature for carrying out the addition reaction is selected from a range from 50 to 60° C., any value within the range from 50 to 60° C. or any sub-range within the range from 50 to 60° C., and the upper limit of the temperature for carrying out the addition reaction is selected from a range from 130 to 150° C., any value within the range from 130 to 150° C. or any sub-range within the range from 130 to 150° C.

Preferably, the oxidation reaction in step 2) is carried out at a reaction temperature ranging from 40 to 120° C., and a reaction pressure ranging from 0.1 to 0.5 MPa.

The lower limit of the temperature for carrying out the oxidation reaction is selected from a range from 40 to 50° C., any value within a range from 40 to 50° C., or a sub-range within the range from 40 to 50° C., and the upper limit of the temperature for carrying out the oxidation reaction is selected from a range from 100 to 120° C., any value within the range from 100 to 120° C., or any sub-range within the range from 100 to 120° C.

Preferably, the oxidant in step 2) is selected from $HNO_3$, nitrite, hydrogen peroxide solution, and any combination thereof.

Preferably, the oxidation catalyst in step 2) is selected from $NH_4VO_3$, $Cu(NO_3)_2$, $Co(NO_3)_2$, $Fe(NO_3)_3$, ammonium molybdate, ammonium tungstate, heteropoly acid and any combination thereof.

Preferably, the molar ratio of the oxidant to the cyclic carboxylic acid ester in step 2) is oxidant:cyclic carboxylic acid ester=3:1 to 15:1; The amount of the oxidation catalyst satisfies that: after the oxidation catalyst is added, the mass concentration of each oxidation catalyst in the oxidation reaction system ranges from 0.01% to 1.0%.

There can be one or more oxidants. When determining the amount thereof, the mass concentration of each oxidant is calculated separately.

Preferably, the intermediate product system comprising the cyclic carboxylic acid ester is a mixed system after the addition reaction is completed or only refers to the cyclic carboxylic acid ester.

Preferably, the method for producing dicarboxylic acid further comprises the step 3):
step 3) after the ring-opening oxidation reaction is completed, separating the lower monocarboxylic acid in the obtained product and recycling the same to the raw material of the addition reaction in step 1).

In a preferred embodiment, the cyclic olefin and carboxylic acid as raw materials are separately fed into a fixed bed reactor loaded with a certain amount of solid catalyst. The reaction pressure ranges from 0.1 to 2.0 MPa, the reaction temperature ranges from 50 to 150° C., the space velocity of cyclic olefin ranges from 0.6 to 3.0 g·g$^{-1}$·h$^{-1}$, the molar ratio of the lower monocarboxylic acid to the cyclic olefin ranges from 0.2 to 10.0. Preferably, the reaction pressure ranges from 0.1 to 1.1 MPa, the reaction temperature ranges from 70 to 125° C., the space velocity of the cyclic olefin ranges from 0.6 to 2.0 g·g$^{-1}$·h$^{-1}$, and the molar ratio of the lower monocarboxylic acid to the cyclic olefin ranges from 1 to 6. After the reaction is completed, the obtained product is separated by distillation to obtain a cyclic carboxylic acid ester product with purity thereof greater than 99.5% or a mixture of a cyclic carboxylic acid ester and a corresponding carboxylic acid.

In a preferred embodiment, the steps of the oxidation reaction are as follows: a certain amount of oxidant is added to the kettle-type reactor and a certain amount of catalyst is added therein, which are then stirred and dissolved at a certain speed (in a range from 100 to 300 rmp/min). The mass concentration of each catalyst in the solution ranges from 0.01% to 1.0%. The temperature of the reactor is raised to the reaction temperature, and then the cyclic carboxylic acid ester or a mixture of the cyclic carboxylic acid ester and the corresponding carboxylic acid is added therein. The reaction temperature ranges from 40 to 120° C., and the molar ratio of nitric acid to cyclic carboxylic acid ester ranges from 3 to 15. After reacting for a time ranging from 10 to 60 minutes, the reaction is stopped. The resulted product is cooled, crystallized and separated, washed and purified to obtain the corresponding dicarboxylic acid.

The benefits achieved by the present application comprises:

1) In the addition-oxidation synthesis route provided in this application, the addition reaction uses the cyclic olefin and the lower monocarboxylic acid as raw materials. The reactants used are mutually soluble so as to conveniently not only increase the ratio of the lower monocarboxylic acid to the cyclic olefin in the reactants, and increase the conversion rate of the cyclic olefin (wherein, the conversion rate of cyclic olefin can reach greater than 95%), but also make the reactant molecules better contact with each other and thus increase the reaction rate.
2) Compared with the carboxylic acid with high-carbon number and weaker acidity, the lower monocarboxylic acid with stronger acidity used in the addition reaction in the present application has increased reaction rate and conversion rate of the addition reaction.
3) The preferred solid acid catalyst in this application has suitable acid strength and acid site distribution, an excellent pore system and a large specific surface area. Therefore, the addition reaction achieves a higher single-pass conversion rate and target product selectivity. The catalyst and the product are easily separated and are less corrosive to the equipment.
4) The addition reaction of this application can be implemented by means of a fixed bed reaction process, and the addition reaction can be operated continuously, which improves the reaction efficiency, and the space-time yield of the reaction can reach greater than 2.0 kg·kg$^{-1}$·h$^{-1}$.
5) In the addition-oxidation synthesis route provided in this application, the product obtained from the addition reaction can be directly used in the subsequent oxidation reaction without separation, which can save separation cost and is more flexible in operation.
6) The corresponding esters produced by the addition reaction of this application are all liquid, which avoids the inconvenience of solid products in the subsequent oxidation reaction.
7) The addition-oxidation synthesis route provided by this application achieves a high yield of dicarboxylic acid. As calculated based on the cyclic olefin, the yield of the corresponding dicarboxylic acid can reach more than 95%.
8) The addition-oxidation synthesis route provided by this application is carried out under mild reaction conditions, and is suitable for continuous and stable large-scale production.

BRIEF DESCRIPTION OF FIGURES

FIG. 1 shows the changes in the conversion rate of cyclohexene and the selectivity of cyclohexyl acetate over time in Example 32.

DETAILED DESCRIPTION

The present invention is described in details by the following Examples, but the invention is not limited to these examples. Unless otherwise specified, the raw materials and catalysts in the examples of the present application are commercially available.

The specific analysis method of the product are as follows:

Analysis of the product obtained from the addition reaction comprises: the composition of the collected product from the addition reaction is quantitatively analyzed by the Agilent 7890B gas chromatograph equipped with FID detector. The gas chromatographic column is selected from FFAP chromatographic column. n-butanol is used as the internal standard for quantitative analysis of the product.

Analysis of the product from the oxidation reaction: the composition of the collected product from the oxidation reaction is quantitatively analyzed by the Maple S6000 liquid chromatography. The liquid chromatographic column is selected from HSS-T3 chromatographic column for analysis.

Example 1

60 m of macroporous strong acid ion exchange resin Amberlyst15 was loaded into the middle of a stainless steel tubular fixed bed reactor, and the upper and lower parts of the middle of the stainless steel tubular fixed bed reactor where the Amberlyst15 catalyst was located were filled with quartz sand respectively. The temperature of the reactor was raised to 90° C., and the reaction pressure was 0.1 MPa. The cyclohexene and acetic acid as reactants were fed into the reactor respectively, wherein the molar ratio of acetic acid to cyclohexene was 4:1. The space velocity of cyclohexene was 1.0 g·g$^{-1}$·h$^{-1}$. The reaction was continuously run for 250 hours. After the reaction product was collected, the composition thereof was analyzed by gas chromatography. The conversion rate of cyclohexene was 85.5%, and the selectivity of cyclohexyl acetate was 98.1%.

The product obtained from the addition reaction was distilled to obtain cyclohexyl acetate with a purity greater than 99.5%. The cyclohexyl acetate was further subjected to an oxidation reaction, and the specific steps of the oxidation reaction were as follows: 145.5 g of 65% nitric acid is added to a 250 ml reactor, and 5.5 g of copper nitrate trihydrate and 0.17 g of ammonium metavanadate as catalysts were added therein respectively. The temperature of the reactor was raised to 70° C. Vigorous stirring was performed to dissolve the catalyst. 17.8 g of cyclohexyl acetate obtained from the addition reaction was added to the reaction solution. The reaction was performed under stirring conditions for 40 minutes. Then the temperature of the reactor was lowered to room temperature to stop the reaction. The composition of the product obtained from the reaction was analyzed by liquid chromatography. The conversion rate of cyclohexyl acetate was 100%, the yield of adipic acid was 96.9%, the yield of glutaric acid was 2.8%, and the yield of succinic acid was 0.1%.

Example 2

60 m of macroporous strong acid ion exchange resin Amberlyst35 was loaded into the middle of a stainless steel tubular fixed bed reactor, and the upper and lower parts of the middle of the stainless steel tubular fixed bed reactor where the Amberlyst35 catalyst was located were filled with quartz sand respectively. The temperature of the reactor was raised to 90° C., and the reaction pressure was 0.1 MPa. The cyclohexene and acetic acid as reactants were fed into the reactor respectively, wherein the molar ratio of acetic acid to cyclohexene was 4:1. The space velocity of cyclohexene was $1.0 \text{ g·g}^{-1}\text{·h}^{-1}$. The reaction was continuously run for 250 hours. After the reaction product was collected, the composition thereof was analyzed by gas chromatography. The conversion rate of cyclohexene was 84.2%, and the selectivity of cyclohexyl acetate was 98.2%.

The product obtained from the addition reaction was distilled to obtain cyclohexyl acetate with a purity greater than 99.5%. The cyclohexyl acetate was further subjected to an oxidation reaction, and the specific steps of the oxidation reaction were as follows: 121.2 g of 65% nitric acid was added to a 250 ml reactor, and 3.7 g of copper nitrate trihydrate and 0.11 g of ammonium metavanadate as catalysts were added therein respectively. The temperature of the reactor was raised to 70° C. Vigorous stirring was performed to dissolve the catalyst. 17.8 g of cyclohexyl acetate obtained from the addition reaction was added to the reaction solution. The reaction was performed under stirring conditions for 40 minutes. Then the temperature of the reactor was lowered to room temperature to stop the reaction. The composition of the product obtained from the reaction was analyzed by liquid chromatography. The conversion rate of cyclohexyl acetate was 100%, the yield of adipic acid was 96.6%, the yield of glutaric acid was 3.1%, and the yield of succinic acid was 0.1%.

Example 3

60 m of macroporous strong acid ion exchange resin Amberlyst36 was loaded into the middle of a stainless steel tubular fixed bed reactor, and the upper and lower parts of the middle of the stainless steel tubular fixed bed reactor where the Amberlyst36 catalyst was located were filled with quartz sand respectively. The temperature of the reactor was raised to 90° C., and the reaction pressure was 0.1 MPa. The cyclohexene and acetic acid as reactants were fed into the reactor respectively, wherein the molar ratio of acetic acid to cyclohexene was 4:1. The space velocity of cyclohexene was $1.0 \text{ g·g}^{-1}\text{·h}^{-1}$. The reaction was continuously run for 250 hours. After the reaction product was collected, the composition thereof was analyzed by gas chromatography. The conversion rate of cyclohexene was 81.5%, and the selectivity of cyclohexyl acetate was 98.1%.

The product obtained from the addition reaction was distilled to obtain cyclohexyl acetate with a purity greater than 99.5%. The cyclohexyl acetate was further subjected to an oxidation reaction, and the specific steps of the oxidation reaction were as follows: 105.0 g of 60% nitric acid is added to a 250 ml reactor, and 2.2 g of copper nitrate trihydrate and 0.07 g of ammonium metavanadate as catalysts were added therein respectively. The temperature of the reactor was raised to 70° C. Vigorous stirring was performed to dissolve the catalyst. 17.8 g of cyclohexyl acetate obtained from the addition reaction was added to the reaction solution. The reaction was performed under stirring conditions for 40 minutes. Then the temperature of the reactor was lowered to room temperature to stop the reaction. The composition of the product obtained from the reaction was analyzed by liquid chromatography. The conversion rate of cyclohexyl acetate was 100%, the yield of adipic acid was 96.1%, the yield of glutaric acid was 3.5%, and the yield of succinic acid was 0.1%.

Example 4

60 m of macroporous strong acid ion exchange resin Amberlyst39 was loaded into the middle of a stainless steel tubular fixed bed reactor, and the upper and lower parts of the middle of the stainless steel tubular fixed bed reactor where the Amberlyst39 catalyst was located were filled with quartz sand respectively. The temperature of the reactor was raised to 90° C., and the reaction pressure was 0.1 MPa. The cyclohexene and acetic acid as reactants were fed into the reactor respectively, wherein the molar ratio of acetic acid to cyclohexene was 4:1. The space velocity of cyclohexene was $1.0 \text{ g·g}^{-1}\text{·h}^{-1}$. The reaction was continuously run for 250 hours. After the reaction product was collected, the composition thereof was analyzed by gas chromatography. The conversion rate of cyclohexene was 81.9%, and the selectivity of cyclohexyl acetate was 98.8%.

The product obtained from the addition reaction was distilled to obtain cyclohexyl acetate with a purity greater than 99.5%. The cyclohexyl acetate was further subjected to an oxidation reaction, and the specific steps of the oxidation reaction were as follows: 78.8 g of 60% nitric acid was added to a 250 ml reactor, and 0.6 g of copper nitrate trihydrate and 0.02 g of ammonium metavanadate as catalysts were added therein respectively. The temperature of the reactor was raised to 70° C. Vigorous stirring was performed to dissolve the catalyst. 17.8 g of cyclohexyl acetate obtained from the addition reaction was added to the reaction solution. The reaction was performed under stirring conditions for 40 minutes. Then the temperature of the reactor was lowered to room temperature to stop the reaction. The composition of the product obtained from the reaction was analyzed by liquid chromatography. The conversion rate of cyclohexyl acetate was 100%, the yield of adipic acid was 94.2%, the yield of glutaric acid was 6.5%, and the yield of succinic acid was 0.4%.

Example 5

60 m of macroporous strong acid ion exchange resin Amberlyst45 was loaded into the middle of a stainless steel tubular fixed bed reactor, and the upper and lower parts of the middle of the stainless steel tubular fixed bed reactor where the Amberlyst45 catalyst was located were filled with quartz sand respectively. The temperature of the reactor was raised to 90° C., and the reaction pressure was 0.1 MPa. The cyclohexene and acetic acid as reactants are fed into the reactor respectively, wherein the molar ratio of acetic acid to cyclohexene was 4:1. The space velocity of cyclohexene was $1.0 \text{ g·g}^{-1}\text{·h}^{-1}$. The reaction was continuously run for 250 hours. After the reaction product was collected, the composition thereof was analyzed by gas chromatography. The conversion rate of cyclohexene was 83.2%, and the selectivity of cyclohexyl acetate was 98.9%.

The product obtained from the addition reaction was distilled to obtain cyclohexyl acetate with a purity greater than 99.5%. The cyclohexyl acetate was further subjected to an oxidation reaction, and the specific steps of the oxidation reaction were as follows: 63.1 g of 50% nitric acid was added to a 250 ml reactor, and 1.0 g of copper nitrate trihydrate and 0.04 g of ammonium metavanadate as catalysts were added therein respectively. The temperature of the reactor was raised to 70° C. Vigorous stirring was performed to dissolve the catalyst. 17.8 g of cyclohexyl acetate obtained from the addition reaction was added to the reaction solution. The reaction was performed under stirring conditions for 40 minutes. Then the temperature of the reactor was lowered to room temperature to stop the reaction. The composition of the product obtained from the reaction was analyzed by liquid chromatography. The conversion rate of cyclohexyl acetate was 100%, the yield of adipic acid was 93.1%, the yield of glutaric acid was 6.0%, and the yield of succinic acid was 0.4%.

Example 6

60 m of macroporous strong acid ion exchange resin Amberlyst 70 was loaded into the middle of a stainless steel tubular fixed bed reactor, and the upper and lower parts of the middle of the stainless steel tubular fixed bed reactor where the Amberlyst 70 catalyst was located were filled with quartz sand respectively. The temperature of the reactor was raised to 90° C., and the reaction pressure was 0.1 MPa. The cyclohexene and acetic acid as reactants were fed into the reactor respectively, wherein the molar ratio of acetic acid to cyclohexene was 4:1. The space velocity of cyclohexene was $1.0 \text{ g·g}^{-1}\text{·h}^{-1}$. The reaction was continuously run for 250 hours. After the reaction product was collected, the composition thereof was analyzed by gas chromatography. The conversion rate of cyclohexene was 82.6%, and the selectivity of cyclohexyl acetate was 98.5%.

The product obtained from the addition reaction was distilled to obtain cyclohexyl acetate with a purity greater than 99.5%. The cyclohexyl acetate was further subjected to an oxidation reaction, and the specific steps of the oxidation reaction are as follows: 87.5 g of 45% nitric acid was added to a 250 ml reactor, and 1.7 g of copper nitrate trihydrate and 0.04 g of ammonium metavanadate as catalysts were added therein respectively. The temperature of the reactor was raised to 70° C. Vigorous stirring was performed to dissolve the catalyst. 17.8 g of cyclohexyl acetate obtained from the addition reaction was added to the reaction solution. The reaction was performed under stirring conditions for 60 minutes. Then the temperature of the reactor was lowered to room temperature to stop the reaction. The composition of the product obtained from the reaction was analyzed by liquid chromatography. The conversion rate of cyclohexyl acetate was 100%, the yield of adipic acid was 95.1%, the yield of glutaric acid was 4.5%, and the yield of succinic acid was 0.3%.

Example 7

60 m of macroporous strong acid ion exchange resin DA330 was loaded into the middle of a stainless steel tubular fixed bed reactor, and the upper and lower parts of the middle of the stainless steel tubular fixed bed reactor where the DA330 catalyst was located were filled with quartz sand respectively. The temperature of the reactor was raised to 90° C., and the reaction pressure was 0.1 MPa. The cyclohexene and acetic acid as reactants were fed into the reactor respectively, wherein the molar ratio of acetic acid to cyclohexene was 4:1. The space velocity of cyclohexene was $1.0 \text{ g·g}^{-1}\text{·h}^{-1}$. The reaction was continuously run for 250 hours.

After the reaction product was collected, the composition thereof was analyzed by gas chromatography. The conversion rate of cyclohexene was 84.5%, and the selectivity of cyclohexyl acetate was 98.5%.

The product obtained from the addition reaction was distilled to obtain cyclohexyl acetate with a purity greater than 99.5%. The cyclohexyl acetate was further subjected to an oxidation reaction, and the specific steps of the oxidation reaction are as follows: 110.3 g of 50% nitric acid is added to a 250 ml reactor, and 1.7 g of copper nitrate trihydrate and 0.08 g of ammonium metavanadate as catalysts are added therein respectively. The temperature of the reactor was raised to 50° C. Vigorous stirring was performed to dissolve the catalyst. 17.8 g of cyclohexyl acetate obtained from the addition reaction was added to the reaction solution. The reaction was performed under stirring conditions for 60 minutes. Then the temperature of the reactor was lowered to room temperature to stop the reaction. The composition of the product obtained from the reaction was analyzed by liquid chromatography. The conversion rate of cyclohexyl acetate was 100%, the yield of adipic acid was 96.5%, the yield of glutaric acid was 3.0%, and the yield of succinic acid was 0.2%.

Example 8

60 m of macroporous strong acid ion exchange resin DNW-II was loaded into the middle of a stainless steel tubular fixed bed reactor, and the upper and lower parts of the middle of the stainless steel tubular fixed bed reactor where the DNW-II catalyst was located were filled with quartz sand respectively. The temperature of the reactor was raised to 90° C., and the reaction pressure was 0.1 MPa. The cyclohexene and acetic acid as reactants were fed into the reactor respectively, wherein the molar ratio of acetic acid to cyclohexene was 4:1. The space velocity of cyclohexene was $1.0 \text{ g·g}^{-1}\text{·h}^{-1}$. The reaction was continuously run for 250 hours. After the reaction product was collected, the composition thereof was analyzed by gas chromatography. The conversion rate of cyclohexene was 83.1%, and the selectivity of cyclohexyl acetate was 98.4%.

The product obtained from the addition reaction was distilled to obtain cyclohexyl acetate with a purity greater than 99.5%. The cyclohexyl acetate was further subjected to an oxidation reaction, and the specific steps of the oxidation reaction were as follows: 110.3 g of 50% nitric acid was added to a 250 ml reactor, and 2.5 g of copper nitrate trihydrate and 0.1 g of ammonium metavanadate as catalysts were added therein respectively. The temperature of the reactor was raised to 40° C. Vigorous stirring was performed to dissolve the catalyst. 17.8 g of cyclohexyl acetate obtained from the addition reaction was added to the reaction solution. The reaction was performed under stirring conditions for 60 minutes. Then the temperature of the reactor was lowered to room temperature to stop the reaction. The composition of the product obtained from the reaction was analyzed by liquid chromatography. The conversion rate of cyclohexyl acetate was 100%, the yield of adipic acid was 96.6%, the yield of glutaric acid was 2.6%, and the yield of succinic acid was 0.3%.

Example 9

60 m of macroporous strong acid ion exchange resin D005 was loaded into the middle of a stainless steel tubular fixed bed reactor, and the upper and lower parts of the middle of the stainless steel tubular fixed bed reactor where the D005 catalyst was located were filled with quartz sand respectively. The temperature of the reactor was raised to 90° C., and the reaction pressure was 0.1 MPa. The cyclohexene and acetic acid as reactants were fed into the reactor respectively, wherein the molar ratio of acetic acid to cyclohexene was 4:1. The space velocity of cyclohexene was 1.0 $g \cdot g^{-1} \cdot h^{-1}$. The reaction was continuously run for 250 hours. After the reaction product was collected, the composition thereof was analyzed by gas chromatography. The conversion rate of cyclohexene was 85.2%, and the selectivity of cyclohexyl acetate was 98.2%.

The product obtained from the addition reaction was distilled to obtain cyclohexyl acetate with a purity greater than 99.5%. The cyclohexyl acetate was further subjected to an oxidation reaction, and the specific steps of the oxidation reaction were as follows: 110.3 g of 50% nitric acid is added to a 250 ml reactor, and 2.5 g of copper nitrate trihydrate and 0.1 g of ammonium metavanadate as catalysts were added therein respectively. The temperature of the reactor was raised to 60° C. Vigorous stirring was performed to dissolve the catalyst. 17.8 g of cyclohexyl acetate obtained from the addition reaction was added to the reaction solution. The reaction was performed under stirring conditions for 40 minutes. Then the temperature of the reactor was lowered to room temperature to stop the reaction. The composition of the product obtained from the reaction was analyzed by liquid chromatography. The conversion rate of cyclohexyl acetate was 100%, the yield of adipic acid was 96.1%, the yield of glutaric acid was 3.0%, and the yield of succinic acid was 0.3%.

Example 10

60 m of macroporous strong acid ion exchange resin HNV-8 was loaded into the middle of a stainless steel tubular fixed bed reactor, and the upper and lower parts of the middle of the stainless steel tubular fixed bed reactor where the HNV-8 catalyst was located were filled with quartz sand respectively. The temperature of the reactor was raised to 90° C., and the reaction pressure was 0.1 MPa. The cyclohexene and acetic acid as reactants were fed into the reactor respectively, wherein the molar ratio of acetic acid to cyclohexene is 4:1. The space velocity of cyclohexene was 1.0 $g \cdot g^{-1} \cdot h^{-1}$. The reaction was continuously run for 250 hours. After the reaction product was collected, the composition thereof was analyzed by gas chromatography. The conversion rate of cyclohexene was 84.6%, and the selectivity of cyclohexyl acetate was 98.3%.

The product obtained from the addition reaction was distilled to obtain cyclohexyl acetate with a purity greater than 99.5%. The cyclohexyl acetate was further subjected to an oxidation reaction, and the specific steps of the oxidation reaction were as follows: 110.3 g of 50% nitric acid is added to a 250 ml reactor, and 2.5 g of copper nitrate trihydrate and 0.1 g of ammonium metavanadate as catalysts were added therein respectively. The temperature of the reactor was raised to 80° C. Vigorous stirring was performed to dissolve the catalyst. 17.8 g of cyclohexyl acetate obtained from the addition reaction was added to the reaction solution. The reaction was performed under stirring conditions for 30 minutes. Then the temperature of the reactor was lowered to room temperature to stop the reaction. The composition of the product obtained from the reaction was analyzed by liquid chromatography. The conversion rate of cyclohexyl acetate was 100%, the yield of adipic acid was 95.1%, the yield of glutaric acid was 3.6%, and the yield of succinic acid was 0.4%.

Example 11

60 ml of the supported phosphotungstic acid catalyst HPW/SiO$_2$ was loaded into the middle of a stainless steel tubular fixed bed reactor, and the upper and lower parts of the middle of the stainless steel tubular fixed bed reactor where the catalyst was located were filled with quartz sand respectively. The temperature of the reactor was raised to 100° C., and the reaction pressure was 2.0 MPa. The cyclohexene and acetic acid as reactants were fed into the reactor respectively, wherein the molar ratio of acetic acid to cyclohexene is 4:1. The space velocity of cyclohexene was 1.0 $g \cdot g^{-1} \cdot h^{-1}$. The reaction was continuously run for 250 hours. After the reaction product was collected, the composition thereof was analyzed by gas chromatography. The conversion rate of cyclohexene was 80.7%, and the selectivity of cyclohexyl acetate was 97.8%.

The product obtained from the addition reaction was distilled to obtain cyclohexyl acetate with a purity greater than 99.5%. The cyclohexyl acetate was further subjected to an oxidation reaction, and the specific steps of the oxidation reaction were as follows: 110.3 g of 50% nitric acid was added to a 250 ml reactor, and 2.5 g of copper nitrate trihydrate and 0.1 g of ammonium metavanadate as catalysts were added therein respectively. The temperature of the reactor was raised to 90° C. Vigorous stirring was performed to dissolve the catalyst. 17.8 g of cyclohexyl acetate obtained from the addition reaction was added to the reaction solution. The reaction was performed under stirring conditions for 30 minutes. Then the temperature of the reactor was lowered to room temperature to stop the reaction. The composition of the product obtained from the reaction was analyzed by liquid chromatography. The conversion rate of cyclohexyl acetate was 100%, the yield of adipic acid was 93.3%, the yield of glutaric acid was 4.1%, and the yield of succinic acid was 0.6%.

Example 12

60 ml of supported phosphomolybdic acid catalyst HPM/SiO$_2$ was loaded into the middle of a stainless steel tubular fixed bed reactor, and the upper and lower parts of the middle of the stainless steel tubular fixed bed reactor where the catalyst was located were filled with quartz sand respectively. The temperature of the reactor was raised to 100° C., and the reaction pressure was 2.0 MPa. The cyclohexene and acetic acid as reactants were fed into the reactor respectively, wherein the molar ratio of acetic acid to cyclohexene was 4:1. The space velocity of cyclohexene was 1.0 $g \cdot g^{-1} \cdot h^{-1}$. The reaction was continuously run for 250 hours. After the reaction product was collected, the composition thereof was analyzed by gas chromatography.

The conversion rate of cyclohexene was 81.2%, and the selectivity of cyclohexyl acetate was 97.6%.

The product obtained from the addition reaction was distilled to obtain cyclohexyl acetate with a purity greater than 99.5%. The cyclohexyl acetate was further subjected to an oxidation reaction, and the specific steps of the oxidation reaction were as follows: 110.3 g of 50% nitric acid was added to a 250 ml reactor, and 2.5 g of copper nitrate trihydrate and 0.1 g of ammonium metavanadate as catalysts were added therein respectively. The temperature of the reactor was raised to 100° C. Vigorous stirring was performed to dissolve the catalyst. 17.8 g of cyclohexyl acetate obtained from the addition reaction was added to the reaction solution.

The reaction was performed under stirring conditions for 30 minutes. Then the temperature of the reactor was lowered to room temperature to stop the reaction. The composition of the product obtained from the reaction was analyzed by liquid chromatography. The conversion rate of cyclohexyl acetate was 100%, the yield of adipic acid was 92.1%, the yield of glutaric acid was 4.6%, and the yield of succinic acid was 0.7%.

Example 13

60 m of supported silicotungstic acid catalyst HSW/SiO$_2$ was loaded into the middle of a stainless steel tubular fixed bed reactor, and the upper and lower parts of the middle of the stainless steel tubular fixed bed reactor where the catalyst was located were filled with quartz sand respectively. The temperature of the reactor was raised to 120° C., and the reaction pressure was 2.0 MPa. The cyclohexene and acetic acid as reactants were fed into the reactor respectively, wherein the molar ratio of acetic acid to cyclohexene was 4:1. The space velocity of cyclohexene was 1.0 g·g$^{-1}$·h$^{-1}$. The reaction was continuously run for 250 hours. After the reaction product was collected, the composition thereof was analyzed by gas chromatography. The conversion rate of cyclohexene was 84.9%, and the selectivity of cyclohexyl acetate was 97.1%.

The product obtained from the addition reaction was distilled to obtain cyclohexyl acetate with a purity greater than 99.5%. The cyclohexyl acetate was further subjected to an oxidation reaction, and the specific steps of the oxidation reaction are as follows: 110.3 g of 50% nitric acid was added to a 250 ml reactor, and 2.5 g of copper nitrate trihydrate and 0.1 g of ammonium metavanadate as catalysts were added therein respectively. The temperature of the reactor was raised to 120° C. Vigorous stirring was performed to dissolve the catalyst. 17.8 g of cyclohexyl acetate obtained from the addition reaction was added to the reaction solution.

The reaction was performed under stirring conditions for 20 minutes. Then the temperature of the reactor was lowered to room temperature to stop the reaction. The composition of the product obtained from the reaction was analyzed by liquid chromatography. The conversion rate of cyclohexyl acetate was 100%, the yield of adipic acid was 90.8%, the yield of glutaric acid was 4.8%, and the yield of succinic acid was 1.0%.

Example 14

60 m of supported silicomolybdic acid catalyst HSM/SiO$_2$ was loaded into the middle of a stainless steel tubular fixed bed reactor, and the upper and lower parts of the middle of the stainless steel tubular fixed bed reactor where the catalyst was located were filled with quartz sand respectively. The temperature of the reactor was raised to 120° C., and the reaction pressure was 2.0 MPa. The cyclohexene and acetic acid as reactants were fed into the reactor respectively, wherein the molar ratio of acetic acid to cyclohexene was 4:1. The space velocity of cyclohexene was 1.0 g·g$^{-1}$·h$^{-1}$. The reaction was continuously run for 250 hours. After the reaction product was collected, the composition thereof was analyzed by gas chromatography. The conversion rate of cyclohexene was 85.4%, and the selectivity of cyclohexyl acetate was 96.9%.

The product obtained from the addition reaction was distilled to obtain cyclohexyl acetate with a purity greater than 99.5%. The cyclohexyl acetate was further subjected to an oxidation reaction, and the specific steps of the oxidation reaction were as follows: 110.3 g of 50% nitric acid was added to a 250 ml reactor, and 3.3 g of cobalt nitrate hexahydrate and 0.1 g of ammonium metavanadate as catalysts were added therein respectively. The temperature of the reactor was raised to 70° C. Vigorous stirring was performed to dissolve the catalyst. 17.8 g of cyclohexyl acetate obtained from the addition reaction was added to the reaction solution. The reaction was performed under stirring conditions for 40 minutes. Then the temperature of the reactor was lowered to room temperature to stop the reaction. The composition of the product obtained from the reaction was analyzed by liquid chromatography. The conversion rate of cyclohexyl acetate was 100%, the yield of adipic acid was 91.2%, the yield of glutaric acid was 6.1%, and the yield of succinic acid was 1.5%.

Example 15

60 m of H$ molecular sieve catalyst was loaded into the middle of a stainless steel tubular fixed bed reactor, and the upper and lower parts of the middle of the stainless steel tubular fixed bed reactor where the catalyst was located were filled with quartz sand respectively. The temperature of the reactor was raised to 80° C., and the reaction pressure was 0.1 MPa. The cyclohexene and acetic acid as reactants were fed into the reactor respectively, wherein the molar ratio of acetic acid to cyclohexene was 4:1. The space velocity of cyclohexene was 1.0 g·g$^{-1}$·h$^{-1}$. The reaction was continuously run for 250 hours. After the reaction product was collected, the composition thereof was analyzed by gas chromatography. The conversion rate of cyclohexene was 75.2%, and the selectivity of cyclohexyl acetate was 98.2%.

The product obtained from the addition reaction was distilled to obtain cyclohexyl acetate with a purity greater than 99.5%. The cyclohexyl acetate is further subjected to an oxidation reaction, and the specific steps of the oxidation reaction were as follows: 110.3 g of 50% nitric acid was added to a 250 ml reactor, and 2.9 g of ferric nitrate and 0.1 g of ammonium metavanadate as catalysts were added therein respectively. The temperature of the reactor was raised to 70° C. Vigorous stirring was performed to dissolve the catalyst. 17.8 g of cyclohexyl acetate obtained from the addition reaction was added to the reaction solution. The reaction was performed under stirring conditions for 40 minutes. Then the temperature of the reactor was lowered to room temperature to stop the reaction. The composition of the product obtained from the reaction was analyzed by liquid chromatography. The conversion rate of cyclohexyl acetate was 100%, the yield of adipic acid was 90.4%, the yield of glutaric acid was 6.9%, and the yield of succinic acid was 1.9%.

Example 16

60 m of HY molecular sieve catalyst was loaded into the middle of a stainless steel tubular fixed bed reactor, and the upper and lower parts of the middle of the stainless steel tubular fixed bed reactor where the catalyst was located were filled with quartz sand respectively. The temperature of the reactor was raised to 80° C., and the reaction pressure was 0.1 MPa. The cyclohexene and acetic acid as reactants were fed into the reactor respectively, wherein the molar ratio of acetic acid to cyclohexene was 4:1. The space velocity of cyclohexene was 1.0 g·g$^{-1}$·h$^{-1}$. The reaction was continuously run for 250 hours. After the reaction product was collected, the composition thereof was analyzed by gas chromatography. The conversion rate of cyclohexene was 62.3%, and the selectivity of cyclohexyl acetate was 98.4%.

The product obtained from the addition reaction was distilled to obtain cyclohexyl acetate with a purity greater than 99.5%. The cyclohexyl acetate was further subjected to an oxidation reaction, and the specific steps of the oxidation reaction were as follows: 99.2 g of 20% hydrogen peroxide was added to a 250 ml reactor, and 2.3 g of phosphomolybdic acid was added therein. The temperature of the reactor was raised to 80° C. Vigorous stirring was performed to dissolve the catalyst. 17.8 g of cyclohexyl acetate obtained from the addition reaction was added to the reaction solution. The reaction was performed under stirring conditions for 60 minutes. Then the temperature of the reactor was lowered to room temperature to stop the reaction. The composition of the product obtained from the reaction was analyzed by liquid chromatography. The conversion rate of cyclohexyl acetate was 100%, the yield of adipic acid was 85.6%, the yield of glutaric acid was 9.8%, and the yield of succinic acid was 2.3%.

Example 17

60 m of HZSM-5 molecular sieve catalyst was loaded into the middle of a stainless steel tubular fixed-bed reactor, and the upper and lower parts of the middle of the stainless steel tubular fixed bed reactor where the catalyst was located were filled with quartz sand respectively. The temperature of the reactor was raised to 80° C., and the reaction pressure was 0.1 MPa. The cyclohexene and acetic acid as reactants were fed into the reactor respectively, wherein the molar ratio of acetic acid to cyclohexene was 4:1. The space velocity of cyclohexene was 1.0 g·g$^{-1}$·h$^{-1}$. The reaction was continuously run for 250 hours. After the reaction product was collected, the composition thereof was analyzed by gas chromatography. The conversion rate of cyclohexene was 71.4%, and the selectivity of cyclohexyl acetate was 98.9%.

The product obtained from the addition reaction was distilled to obtain cyclohexyl acetate with a purity greater than 99.5%. The cyclohexyl acetate was further subjected to an oxidation reaction, and the specific steps of the oxidation reaction were as follows: 99.2 g of 20% hydrogen peroxide was added to a 250 ml reactor, and 3.8 g of ammonium tungstate was added therein. The temperature of the reactor was raised to 80° C. Vigorous stirring was performed to dissolve the catalyst. 17.8 g of cyclohexyl acetate obtained from the addition reaction was added to the reaction solution. The reaction was performed under stirring conditions for 60 minutes. Then the temperature of the reactor was lowered to room temperature to stop the reaction. The composition of the product obtained from the reaction was analyzed by liquid chromatography. The conversion rate of cyclohexyl acetate was 100%, the yield of adipic acid was 82.1%, the yield of glutaric acid was 10.4%, and the yield of succinic acid was 3.6%.

Example 18

60 m of macroporous strong acid ion exchange resin Amberlyst 45 was loaded into the middle of the stainless steel tubular fixed bed reactor, and the upper and lower parts of the middle of the stainless steel tubular fixed bed reactor where the Amberlyst 45 catalyst was located were filled with quartz sand respectively. The temperature of the reactor was increased to 120° C., and the reaction pressure was 2.0 MPa. The cyclohexene and acetic acid as reactants were fed into the reactor respectively, wherein the molar ratio of acetic acid to cyclohexene was 4:1. The space velocity of cyclohexene was 1.0 g·g$^{-1}$·h$^{-1}$. The reaction was continuously run for 250 hours. After the reaction product was collected, the composition thereof was analyzed by gas chromatography. The conversion rate of cyclohexene was 85.5%, and the selectivity of cyclohexyl acetate was 98.1%.

The unreacted cyclohexene was separated from the product obtained from the addition reaction to obtain a mixture mainly comprising acetic acid and cyclohexyl acetate, wherein the molar ratio of acetic acid to cyclohexyl acetate was 3.7. The mixture of acetic acid/cyclohexyl acetate was further subjected to an oxidation reaction, and the specific steps of the oxidation reaction were as follows: 110.3 g of 50% nitric acid was added to a 250 ml reactor, and 2.5 g of copper nitrate trihydrate and 0.1 g of ammonium metavanadate were added therein respectively. The temperature of the reactor was raised to 70° C. Vigorous stirring was performed to dissolve the catalyst. 45.7 g of the above-mentioned mixture of acetic acid/cyclohexyl acetate was added to the reaction solution. The reaction was performed under stirring conditions for 40 minutes. Then the temperature of the reactor was lowered to room temperature to stop the reaction. The composition of the product obtained from the reaction was analyzed by liquid chromatography. The conversion rate of cyclohexyl acetate was 100%, the yield of adipic acid was 96.1%, the yield of glutaric acid was 3.1%, and the yield of succinic acid was 0.2%.

Example 19

60 m of macroporous strong acid ion exchange resin DNW-II was loaded into the middle of the stainless steel tubular fixed bed reactor, and the upper and lower parts of the middle of the stainless steel tubular fixed bed reactor where the DNW-II catalyst was located were filled with quartz sand respectively. The temperature of the reactor was increased to 140° C., and the reaction pressure was 2.0 MPa. The cyclohexene and acetic acid as reactants were fed into the reactor respectively, wherein the molar ratio of acetic acid to cyclohexene was 6:1. The space velocity of cyclohexene was 2.0 g·g$^{-1}$·h$^{-1}$. The reaction was continuously run for 250 hours. After the reaction product was collected, the composition thereof was analyzed by gas chromatography. The conversion rate of cyclohexene was 81.1%, and the selectivity of cyclohexyl acetate was 98.5%.

The unreacted cyclohexene was separated from the product obtained from the addition reaction to obtain a mixture mainly comprising acetic acid and cyclohexyl acetate, wherein the molar ratio of acetic acid to cyclohexyl acetate was 6.4. The mixture of acetic acid/cyclohexyl acetate was further subjected to an oxidation reaction, and the specific steps of the oxidation reaction were as follows: 110.3 g of 50% nitric acid was added to a 250 ml reactor, and 2.5 g of copper nitrate trihydrate and 0.1 g of ammonium metavanadate were added therein respectively. The temperature of the reactor was raised to 70° C. Vigorous stirring was performed to dissolve the catalyst. 66.3 g of the above-mentioned mixture of acetic acid/cyclohexyl acetate was added to the reaction solution. The reaction was performed under stirring conditions for 40 minutes. Then the temperature of the reactor was lowered to room temperature to stop the reaction. The composition of the product obtained from the reaction was analyzed by liquid chromatography. The conversion rate of cyclohexyl acetate was 100%, the yield of adipic acid was 96.4%, the yield of glutaric acid was 3.0%, and the yield of succinic acid was 0.1%.

Example 20

60 m of macroporous strong acid ion exchange resin Amberlyst70 was loaded into the middle of a stainless steel tubular fixed bed reactor, and the upper and lower parts of the middle of the stainless steel tubular fixed bed reactor where the Amberlyst70 catalyst was located were filled with quartz sand respectively. The temperature of the reactor was increased to 150° C., and the reaction pressure was 2.0 MPa. The cyclohexene and acetic acid as reactants were fed into the reactor respectively, wherein the molar ratio of acetic acid to cyclohexene was 6:1. The space velocity of cyclohexene was 3.0 $g \cdot g^{-1} \cdot h^{-1}$. The reaction was continuously run for 250 hours. After the reaction product was collected, the composition thereof was analyzed by gas chromatography. The conversion rate of cyclohexene was 78.2%, and the selectivity of cyclohexyl acetate was 98.2%.

The product obtained from the addition reaction was distilled to obtain cyclohexyl acetate with a purity greater than 99.5%. The cyclohexyl acetate was further subjected to an oxidation reaction. The specific steps of the reaction were as follows: 110.3 g of 50% nitric acid was added into a 250 ml reactor, and 1.1 g $(NH_4)_6 Mo_7O_{24}$ and 0.1 g ammonium metavanadate were added therein respectively. The temperature of the reactor was raised to 70° C. Vigorous stirring was performed to dissolve the catalyst. 17.8 g of cyclohexyl acetate obtained from the addition reaction was added to the reaction solution. The reaction was performed under stirring conditions for 40 minutes. Then the temperature of the reactor was lowered to room temperature to stop the reaction. The composition of the product obtained from the reaction was analyzed by liquid chromatography. The conversion rate of cyclohexyl acetate was 100%, the yield of adipic acid was 93.1%, the yield of glutaric acid was 5.5%, and the yield of succinic acid was 0.7%.

Example 21

60 m of the catalyst aluminum trichloride supported by silica ($AlCl_3$—$SiO_2$) was loaded into the middle of a stainless steel tubular fixed bed reactor, and the upper and lower parts of the middle of a stainless steel tubular fixed bed reactor where the catalyst was located were respectively filled with quartz sand. The temperature of the reactor was increased to 150° C., and the reaction pressure was 2.0 MPa. The cyclohexene and acetic acid as reactants were fed into the reactor respectively, wherein the molar ratio of acetic acid to cyclohexene was 6:1. The space velocity of cyclohexene was 0.6 $g \cdot g^{-1} \cdot h^{-1}$. The reaction was continuously run for 250 hours. After the reaction product was collected, the composition thereof was analyzed by gas chromatography. The conversion rate of cyclohexene was 50.3%, and the selectivity of cyclohexyl acetate was 97.6%.

The product obtained from the addition reaction was distilled to obtain cyclohexyl acetate with a purity greater than 99.5%. The cyclohexyl acetate was further subjected to an oxidation reaction. The specific steps of the reaction were as follows: 110.3 g of 50% nitric acid was added into a 250 ml reactor, and 1.4 g $(NH_4)_2 MoO_4$ and 0.1 g ammonium metavanadate were added therein respectively. The temperature of the reactor was raised to 70° C. Vigorous stirring was performed to dissolve the catalyst. 17.8 g of cyclohexyl acetate obtained from the addition reaction was added to the reaction solution. The reaction was performed under stirring conditions for 40 minutes. Then the temperature of the reactor was lowered to room temperature to stop the reaction. The composition of the product obtained from the reaction was analyzed by liquid chromatography. The conversion rate of cyclohexyl acetate was 100%, the yield of adipic acid was 93.4%, the yield of glutaric acid was 5.2%, and the yield of succinic acid was 0.7%.

Example 22

60 m of macroporous strong acid ion exchange resin DA330 was loaded into the middle of the stainless steel tubular fixed bed reactor, and the upper and lower parts of the middle of the stainless steel tubular fixed bed reactor where the DA330 catalyst was located were filled with quartz sand respectively. The temperature of the reactor was increased to 100° C., and the reaction pressure was 2.0 MPa. The cyclohexene and acetic acid as reactants were fed into the reactor respectively, wherein the molar ratio of acetic acid to cyclohexene was 2:1. The space velocity of cyclohexene was 2.0 $g \cdot g^{-1} \cdot h^{-1}$. The reaction was continuously run for 250 hours. After the reaction product was collected, the composition thereof was analyzed by gas chromatography. The conversion rate of cyclohexene was 76.5%, and the selectivity of cyclohexyl acetate was 98.6%.

The unreacted cyclohexene was separated from the product obtained from the addition reaction to obtain a mixture mainly comprising acetic acid and cyclohexyl acetate, wherein the molar ratio of acetic acid to cyclohexyl acetate was 1.6. The mixture of acetic acid/cyclohexyl acetate was further subjected to an oxidation reaction, and the specific steps of the oxidation reaction were as follows: 110.3 g of 50% nitric acid was added to a 250 ml reactor, and 2.5 g of copper nitrate trihydrate and 0.1 g of ammonium metavanadate were added therein respectively. The temperature of the reactor was raised to 70° C. Vigorous stirring was performed to dissolve the catalyst. 30.0 g of the above-mentioned mixture of acetic acid/cyclohexyl acetate was added to the reaction solution. The reaction was performed under stirring conditions for 40 minutes. Then the temperature of the reactor was lowered to room temperature to stop the reaction. The composition of the product obtained from the reaction was analyzed by liquid chromatography. The conversion rate of cyclohexyl acetate was 100%, the yield of adipic acid was 96.9%, the yield of glutaric acid was 2.7%, and the yield of succinic acid was 0.1%.

Example 23

60 m of macroporous strong acid ion exchange resin D 005 was loaded into the middle of the stainless steel tubular fixed bed reactor, and the upper and lower parts of the middle of the stainless steel tubular fixed bed reactor where the D 005 catalyst was located were filled with quartz sand respectively. The temperature of the reactor was increased to 50° C., and the reaction pressure was 1.0 MPa. The cyclohexene and acetic acid as reactants were fed into the reactor respectively, wherein the molar ratio of acetic acid to cyclohexene was 4:1. The space velocity of cyclohexene was 1.0 $g \cdot g^{-1} \cdot h^{-1}$. The reaction was continuously run for 250 hours. After the reaction product was collected, the composition thereof was analyzed by gas chromatography. The conversion rate of cyclohexene was 67.2%, and the selectivity of cyclohexyl acetate was 98.2%.

The product obtained from the addition reaction was distilled to obtain cyclohexyl acetate with a purity greater than 99.5%. The cyclohexyl acetate was further subjected to an oxidation reaction, and the specific steps of the oxidation reaction were as follows: 110.3 g of 50% nitric acid was added to a 250 ml reactor, and 2.5 g of copper nitrate trihydrate was added therein. The temperature of the reactor was raised to 70° C. Vigorous stirring was performed to dissolve the catalyst. 17.8 g of cyclohexyl acetate obtained from the addition reaction was added to the reaction solution. The reaction was performed under stirring conditions for 40 minutes. Then the temperature of the reactor was lowered to room temperature to stop the reaction. The composition of the product obtained from the reaction was analyzed by liquid chromatography. The conversion rate of cyclohexyl acetate was 100%, the yield of adipic acid was 83.3%, the yield of glutaric acid was 12.4%, and the yield of succinic acid was 2.5%.

Example 24

60 m of macroporous strong acid ion exchange resin Amberlyst45 was loaded into the middle of the stainless steel tubular fixed bed reactor, and the upper and lower parts of the middle of the stainless steel tubular fixed bed reactor where the Amberlyst45 catalyst was located were filled with quartz sand respectively. The temperature of the reactor was increased to 80° C., and the reaction pressure was 0.1 MPa. The cyclohexene and acetic acid as reactants were fed into the reactor respectively, wherein the molar ratio of acetic acid to cyclohexene was 0.5:1. The space velocity of cyclohexene was 0.8 g·g$^{-1}$·h$^{-1}$. The reaction was continuously run for 250 hours. After the reaction product was collected, the composition thereof was analyzed by gas chromatography. The conversion rate of cyclohexene was 39.6%, and the selectivity of cyclohexyl acetate was 98.6%.

The product obtained from the addition reaction was distilled to obtain cyclohexyl acetate with a purity greater than 99.5%. The cyclohexyl acetate was further subjected to an oxidation reaction, and the specific steps of the oxidation reaction were as follows: 110.3 g of 50% nitric acid was added to a 250 ml reactor, and 0.1 g of ammonium metavanadate was added therein. The temperature of the reactor was raised to 70° C. Vigorous stirring was performed to dissolve the catalyst. 17.8 g of cyclohexyl acetate obtained from the addition reaction was added to the reaction solution. The reaction was performed under stirring conditions for 40 minutes. Then the temperature of the reactor was lowered to room temperature to stop the reaction. The composition of the product obtained from the reaction was analyzed by liquid chromatography. The conversion rate of cyclohexyl acetate was 100%, the yield of adipic acid was 81.2%, the yield of glutaric acid was 13.5%, and the yield of succinic acid was 2.6%.

Example 25

60 m of macroporous strong acid ion exchange resin Amberlyst45 was loaded into the middle of the stainless steel tubular fixed bed reactor, and the upper and lower parts of the middle of the stainless steel tubular fixed bed reactor where the Amberlyst45 catalyst was located were filled with quartz sand respectively. The temperature of the reactor was increased to 80° C., and the reaction pressure was 0.1 MPa. The cyclohexene and acetic acid as reactants were fed into the reactor respectively, wherein the molar ratio of acetic acid to cyclohexene was 0.2:1. The space velocity of cyclohexene was 0.6 g·g$^{-1}$·h$^{-1}$. The reaction was continuously run for 250 hours. After the reaction product was collected, the composition thereof was analyzed by gas chromatography. The conversion rate of cyclohexene was 17.5%, and the selectivity of cyclohexyl acetate was 98.7%.

The product obtained from the addition reaction was distilled to obtain cyclohexyl acetate with a purity greater than 99.5%. The cyclohexyl acetate was further subjected to an oxidation reaction, and the specific steps of the oxidation reaction were as follows: 110.3 g of 50% nitric acid was added to a 250 ml reactor, and 2.5 g of copper nitrate trihydrate and 0.1 g of ammonium metavanadate were added therein respectively. The temperature of the reactor was raised to 70° C. Vigorous stirring was performed to dissolve the catalyst. 17.8 g of cyclohexyl acetate obtained from the addition reaction was added to the reaction solution. The reaction was performed under stirring conditions for 40 minutes. Then the temperature of the reactor was lowered to room temperature to stop the reaction. The composition of the product obtained from the reaction was analyzed by liquid chromatography. The conversion rate of cyclohexyl acetate was 100%, the yield of adipic acid was 96.7%, the yield of glutaric acid was 2.7%, and the yield of succinic acid was 0.1%.

Example 26

60 m of macroporous strong acid ion exchange resin DNW-II was loaded into the middle of the stainless steel tubular fixed bed reactor, and the upper and lower parts of the middle of the stainless steel tubular fixed bed reactor where the DNW-II catalyst was located were filled with quartz sand respectively. The temperature of the reactor was increased to 80° C., and the reaction pressure was 0.1 MPa. The cyclopentene and acetic acid as reactants were fed into the reactor respectively, wherein the molar ratio of acetic acid to cyclopentene was 4:1. The space velocity of cyclopentene was 1.0 g·g$^{-1}$·h$^{-1}$. The reaction was continuously run for 250 hours. After the reaction product was collected, the composition thereof was analyzed by gas chromatography. The conversion rate of cyclopentene was 81.2%, and the selectivity of cyclopentyl acetate was 98.2%.

The product obtained from the addition reaction was distilled to obtain cyclopentyl acetate with a purity greater than 99.5%. The cyclopentyl acetate was further subjected to an oxidation reaction, and the specific steps of the oxidation reaction were as follows: 110.3 g of 50% nitric acid was added to a 250 ml reactor, and 2.5 g of copper nitrate trihydrate and 0.1 g of ammonium metavanadate were added therein respectively. The temperature of the reactor was raised to 70° C. Vigorous stirring was performed to dissolve the catalyst. 16.0 g of cyclopentyl acetate obtained from the addition reaction was added to the reaction solution. The reaction was performed under stirring conditions for 40 minutes. Then the temperature of the reactor was lowered to room temperature to stop the reaction. The composition of the product obtained from the reaction was analyzed by liquid chromatography. The conversion rate of cyclopentyl acetate was 100%, the yield of glutaric acid was 96.7%, and the yield of succinic acid was 2.9%.

Example 27

60 m of macroporous strong acid ion exchange resin Amberlyst45 was loaded into the middle of a stainless steel tubular fixed bed reactor, and the upper and lower parts of the middle of the stainless steel tubular fixed bed reactor where the Amberlyst45 catalyst was located were filled with quartz sand respectively. The temperature of the reactor was raised to 80° C., and the reaction pressure was 0.1 MPa. The mixture of cyclohexene and acetic acid as reactants were fed into the reactor, wherein the molar ratio of acetic acid to cyclohexene is 10:1. The space velocity of cyclohexene was 1.0 g·g$^{-1}$·h$^{-1}$. The reaction was continuously run for 250 hours. After the reaction product was collected, the composition thereof was analyzed by gas chromatography. The conversion of cyclohexene was 96.4%, and the selectivity of cyclohexyl acetate was 98.3%.

The product obtained from the addition reaction was distilled to obtain cyclohexyl acetate with a purity greater than 99.5%. The cyclohexyl acetate was further subjected to an oxidation reaction, and the specific steps of the oxidation reaction were as follows: 78.8 g of 50% nitric acid was added to a 250 ml reactor, and 0.96 g of copper nitrate trihydrate and 0.07 g of ammonium metavanadate were added therein respectively. The temperature of the reactor was raised to 70° C. Vigorous stirring was performed to dissolve the catalyst. 17.8 g of cyclohexyl acetate obtained from the addition reaction was added to the reaction solution. The reaction was performed under stirring conditions for 40 minutes. Then the temperature of the reactor was lowered to room temperature to stop the reaction. The composition of the product obtained from the reaction was analyzed by liquid chromatography. The conversion rate of cyclohexyl acetate was 100%, the yield of adipic acid was 96.5%, the yield of glutaric acid was 2.9%, and the yield of succinic acid was 0.4%.

Example 28

60 m of macroporous strong acid ion exchange resin Amberlyst45 was loaded into the middle of a stainless steel tubular fixed bed reactor, and the upper and lower parts of the middle of the stainless steel tubular fixed bed reactor where the Amberlyst45 catalyst was located were filled with quartz sand respectively. The temperature of the reactor was raised to 100° C., and the reaction pressure was 0.1 MPa. The cycloheptene and formic acid as reactants were fed into the reactor, wherein the molar ratio of formic acid to cycloheptene was 4:1. The space velocity of cycloheptene was 1.0 g·g$^{-1}$·h$^{-1}$. The reaction was continuously run for 250 hours. After the reaction product was collected, the composition thereof was analyzed by gas chromatography. The conversion of cycloheptene was 85.3%, and the selectivity of cycloheptyl formate was 98.5%.

The product obtained from the addition reaction was distilled to obtain cycloheptyl formate with a purity greater than 99.5%. The cycloheptyl formate was further subjected to an oxidation reaction, and the specific steps of the oxidation reaction were as follows: 110.3 g of 50% nitric acid was added to a 250 ml reactor, and 2.5 g of copper nitrate trihydrate and 0.1 g of ammonium metavanadate were added therein respectively. The temperature of the reactor was raised to 70° C. Vigorous stirring was performed to dissolve the catalyst. 17.8 g of cycloheptyl formate obtained from the addition reaction was added to the reaction solution. The reaction was performed under stirring conditions for 40 minutes. Then the temperature of the reactor was lowered to room temperature to stop the reaction. The composition of the product obtained from the reaction was analyzed by liquid chromatography. The conversion rate of cycloheptyl formate was 100%, the yield of pimelic acid was 95.6%, the yield of adipic acid was 3.4%, and the yield of glutaric acid was 0.5%.

Example 29

60 m of macroporous strong acid ion exchange resin Amberlyst45 was loaded into the middle of a stainless steel tubular fixed bed reactor, and the upper and lower parts of the middle of the stainless steel tubular fixed bed reactor where the Amberlyst45 catalyst was located were filled with quartz sand respectively. The temperature of the reactor was raised to 100° C., and the reaction pressure was 0.1 MPa. The cyclohexene and acrylic acid as reactants were fed into the reactor, wherein the molar ratio of acrylic acid to cyclohexene was 4:1. The space velocity of cyclohexene was 1.0 g·g$^{-1}$·h$^{-1}$. The reaction was continuously run for 250 hours. After the reaction product was collected, the composition thereof was analyzed by gas chromatography. The conversion of cyclohexene was 84.3%, and the selectivity of cyclohexyl acrylate was 98.6%.

The product obtained from the addition reaction was distilled to obtain cyclohexyl acrylate with a purity greater than 99.5%. The cyclohexyl acrylate was further subjected to an oxidation reaction, and the specific steps of the oxidation reaction were as follows: 110.3 g of 50% nitric acid was added to a 250 ml reactor, and 2.5 g of copper nitrate trihydrate and 0.1 g of ammonium metavanadate were added therein respectively. The temperature of the reactor was raised to 70° C. Vigorous stirring was performed to dissolve the catalyst. 19.3 g of cyclohexyl acrylate obtained from the addition reaction was added to the reaction solution. The reaction was performed under stirring conditions for 40 minutes. Then the temperature of the reactor was lowered to room temperature to stop the reaction. The composition of the product obtained from the reaction was analyzed by liquid chromatography. The conversion rate of cyclohexyl acrylate was 100%, the yield of adipic acid was 95.1%, the yield of glutaric acid was 3.5%, and the yield of succinic acid was 0.6%.

Example 30

60 m of macroporous strong acid ion exchange resin Amberlyst45 was loaded into the middle of a stainless steel tubular fixed bed reactor, and the upper and lower parts of the middle of the stainless steel tubular fixed bed reactor where the Amberlyst45 catalyst was located were filled with quartz sand respectively. The temperature of the reactor was raised to 100° C., and the reaction pressure was 0.1 MPa. The mixture of cyclohexene and trifluoroacetic acid as reactants were fed into the reactor, wherein the molar ratio of trifluoroacetic acid to cyclohexene was 4:1. The space velocity of cyclohexene was 1.0 g·g$^{-1}$·h$^{-1}$. The reaction was continuously run for 250 hours. After the reaction product was collected, the composition thereof was analyzed by gas chromatography. The conversion of cyclohexene was 86.3%, and the selectivity of cyclohexyl trifluoroacetate was 98.5%.

The product obtained from the addition reaction was distilled to obtain cyclohexyl trifluoroacetate with a purity greater than 99.5%. The cyclohexyl trifluoroacetate was further subjected to an oxidation reaction, and the specific steps of the oxidation reaction were as follows: 110.3 g of 50% nitric acid was added to a 250 ml reactor, and 2.5 g of copper nitrate trihydrate and 0.1 g of ammonium metavanadate were added therein respectively. The temperature of the reactor was raised to 70° C. Vigorous stirring was performed to dissolve the catalyst. 24.5 g of cyclohexyl trifluoroacetate obtained from the addition reaction was added to the reaction solution. The reaction was performed under stirring conditions for 40 minutes. Then the temperature of the reactor was lowered to room temperature to stop the reaction. The composition of the product obtained from the reaction was analyzed by liquid chromatography. The conversion rate of cyclohexyl trifluoroacetate was 100%, the yield of adipic acid was 95.8%, the yield of glutaric acid was 3.3%, and the yield of succinic acid was 0.1%.

Example 31

60 m of macroporous strong acid ion exchange resin Amberlyst45 was loaded into the middle of a stainless steel tubular fixed bed reactor, and the upper and lower parts of the middle of the stainless steel tubular fixed bed reactor where the Amberlyst45 catalyst was located were filled with quartz sand respectively. The temperature of the reactor was raised to 100° C., and the reaction pressure was 0.1 MPa. The 3-chlorocyclohexene and acetic acid as reactants were fed into the reactor, wherein the molar ratio of acetic acid to 3-chlorocyclohexene was 4:1. The space velocity of 3-chlorocyclohexene was 1.0 $g \cdot g^{-1} \cdot h^{-1}$. The reaction was continuously run for 250 hours. After the reaction product was collected, the composition thereof was analyzed by gas chromatography. The conversion of 3-chlorocyclohexene was 80.1%, and the selectivity of chlorocyclohexyl acetate was 98.1%.

The product obtained from the addition reaction was distilled to obtain chlorocyclohexyl acetate with a purity greater than 99.5%. The chlorocyclohexyl acetate was further subjected to an oxidation reaction, and the specific steps of the oxidation reaction were as follows: 110.3 g of 50% nitric acid was added to a 250 ml reactor, and 2.5 g of copper nitrate trihydrate and 0.1 g of ammonium metavanadate were added therein respectively. The temperature of the reactor was raised to 70° C. Vigorous stirring was performed to dissolve the catalyst. 22.1 g of chlorocyclohexyl acetate obtained from the addition reaction was added to the reaction solution. The reaction was performed under stirring conditions for 40 minutes. Then the temperature of the reactor was lowered to room temperature to stop the reaction. The composition of the product obtained from the reaction was analyzed by liquid chromatography. The conversion rate of chlorocyclohexyl acetate was 100%, the yield of chloroadipic acid was 96.2%, the yield of glutaric acid was 3.0%, and the yield of succinic acid was 0.1%.

Example 32

60 m of macroporous strong acid ion exchange resin Amberlyst45 was loaded into the middle of a stainless steel tubular fixed bed reactor, and the upper and lower parts of the middle of the stainless steel tubular fixed bed reactor where the Amberlyst45 catalyst was located were filled with quartz sand respectively. The temperature of the reactor was raised to 100° C., and the reaction pressure was 0.1 MPa. The mixture of methylcyclohexene and acetic acid as reactants were fed into the reactor, wherein the molar ratio of acetic acid to methylcyclohexene was 4:1. The space velocity of methylcyclohexene was 1.0 $g \cdot g^{-1} \cdot h^{-1}$. The reaction was continuously run for 250 hours. After the reaction product was collected, the composition thereof was analyzed by gas chromatography. The conversion of methylcyclohexene was 83.2%, and the selectivity of methylcyclohexyl acetate was 98.5%.

The product obtained from the addition reaction was distilled to obtain methylcyclohexyl acetate with a purity greater than 99.5%. The methylcyclohexyl acetate was further subjected to an oxidation reaction, and the specific steps of the oxidation reaction were as follows: 110.3 g of 50% nitric acid was added to a 250 ml reactor, and 2.5 g of copper nitrate trihydrate and 0.1 g of ammonium metavanadate were added therein respectively. The temperature of the reactor was raised to 70° C. Vigorous stirring was performed to dissolve the catalyst. 19.5 g of methylcyclohexyl acetate obtained from the addition reaction was added to the reaction solution. The reaction was performed under stirring conditions for 40 minutes. Then the temperature of the reactor was lowered to room temperature to stop the reaction. The composition of the product obtained from the reaction was analyzed by liquid chromatography. The conversion rate of methylcyclohexyl acetate was 100%, the yield of methyl adipic acid was 96.4%, the yield of glutaric acid was 2.9%, and the yield of succinic acid was 0.1%.

Example 33

10 m of macroporous strong acid ion exchange resin Amberlyst45 was loaded into a stainless steel reactor, and then 20 g cyclohexene and 56 g acetic acid were fed into the reactor. After the reactor was sealed, the temperature therein was raised to 100° C. The reaction was stopped after continuous heating and stirring for 4 hours. Then the temperature in the reactor was lowered to room temperature. The reaction product was taken out from the reactor, and the composition thereof was analyzed by gas chromatography. The conversion of cyclohexene was 91.2%, and the selectivity of cyclohexyl acetate was 98.2%.

The product obtained from the addition reaction was distilled to obtain cyclohexyl acetate with a purity greater than 99.5%. The cyclohexyl acetate was further subjected to an oxidation reaction, and the specific steps of the oxidation reaction were as follows: 78.8 g of 50% nitric acid was added to a 250 ml reactor, and 0.48 g of copper nitrate trihydrate and 0.07 g of ammonium metavanadate were added therein respectively. The temperature of the reactor was raised to 60° C. Vigorous stirring was performed to dissolve the catalyst. 17.8 g of cyclohexyl acetate obtained from the addition reaction was added to the reaction solution. The reaction was performed under stirring conditions for 60 minutes. Then the temperature of the reactor was lowered to room temperature to stop the reaction. The composition of the product obtained from the reaction was analyzed by liquid chromatography. The conversion rate of cyclohexyl acetate was 100%, the yield of adipic acid was 96.1%, the yield of glutaric acid was 3.1%, and the yield of succinic acid was 0.5%.

Example 34

60 m of macroporous strong acid ion exchange resin Amberlyst45 was loaded into the middle of a stainless steel tubular fixed bed reactor, and the upper and lower parts of the middle of the stainless steel tubular fixed bed reactor where the Amberlyst45 catalyst was located were filled with quartz sand respectively. The temperature of the reactor was raised to 90° C., and the reaction pressure was 0.1 MPa. The cyclohexene and acetic acid as reactants were fed into the reactor respectively, wherein the molar ratio of acetic acid to cyclohexene was 4:1. The space velocity of cyclohexene was 1.0 $g \cdot g^{-1} \cdot h^{-1}$. The reaction was continuously run for 1000 hours. After the reaction product was collected, the composition thereof was analyzed by gas chromatography. The conversion of cyclohexene was in a range from 83% to 84%, and the selectivity of cyclohexyl acetate was in a range from 98% to 99%. The result of the reaction is shown in FIG. 1.

The product obtained from the addition reaction was distilled to obtain cyclohexyl acetate with a purity greater than 99.5%. The cyclohexyl acetate was further subjected to an oxidation reaction, and the specific steps of the oxidation reaction were as follows: 110.3 g of 50% nitric acid was added to a 250 ml reactor, and 2.5 g of copper nitrate trihydrate and 0.1 g of ammonium metavanadate were added therein respectively. The temperature of the reactor was raised to 70° C. Vigorous stirring was performed to dissolve the catalyst. 17.8 g of cyclohexyl acetate obtained from the addition reaction was added to the reaction solution. The reaction was performed under stirring conditions for 40 minutes. Then the temperature of the reactor was lowered to room temperature to stop the reaction. The composition of the product obtained from the reaction was analyzed by liquid chromatography. The conversion rate of cyclohexyl acetate was 100%, the yield of adipic acid was 96.8%, the yield of glutaric acid was 2.6%, and the yield of succinic acid was 0.1%.

Comparative Example 1

60 m of macroporous strong acid ion exchange resin Amberlyst45 was loaded into the middle of a stainless steel tubular fixed bed reactor, and the upper and lower parts of the middle of the stainless steel tubular fixed bed reactor where the Amberlyst45 catalyst was located were filled with quartz sand respectively. The temperature of the reactor was raised to 90° C., and the reaction pressure was 0.1 MPa. The cyclohexene and hexanoic acid as reactants were fed into the reactor, wherein the molar ratio of hexanoic acid to cyclohexene was 4:1. The space velocity of cyclohexene was 1.0 g·g$^{-1}$·h$^{-1}$. The reaction was continuously run for 24 hours. After the reaction product was collected, the composition thereof was analyzed by gas chromatography. The conversion of cyclohexene was 64.1%, and the selectivity of cyclohexyl hexanoate was 98.1%. When hexanoic acid was used as reactant, the conversion rate achieved by the addition reaction was significantly lower than that achieved in Example 5 under the same conditions.

Though the present application has been described above with reference to preferred examples, these examples are not intended to limit the present application. Without departing from the spirit of the present application, the skilled in the art will be able to make several possible variations or modifications, which are equivalent examples and fall within the protection scope of the technical solutions of the present application.

The invention claimed is:
1. A method for producing dicarboxylic acid, comprising the following steps:
1) obtaining an intermediate product system comprising cyclic carboxylic acid ester from a raw material system comprising a cyclic olefin and a lower monocarboxylic acid by an addition reaction in the presence of an addition reaction catalyst; and
2) carrying out a ring-opening oxidation reaction in the presence of an oxidant and an oxidation catalyst to produce a corresponding dicarboxylic acid product from the intermediate product system;
wherein the lower monocarboxylic acid is selected from at least one compounds with a chemical formula represented by formula V:

Formula V wherein, $R_{501}$ is selected from H, $C_1$ to $C_3$ hydrocarbon group or $C_1$ to $C_3$ halogenated hydrocarbon group;
wherein the addition reaction catalyst in step 1) comprises at least one of a supported inorganic acid catalyst, a cation exchange resin, and a molecular sieve;
wherein the supported inorganic acid catalyst contains an inorganic acid and a support;
wherein the inorganic acid is selected from at least one of sodium hydrogen sulfate, sodium hydrogen phosphate, AlCl$_3$ and heteropoly acid, and the support is selected from at least one of silica, diatomite and kaolin; and
wherein the weight percentage of the inorganic acid in the supported inorganic acid ranges from 5% to 25%;
wherein the cation exchange resin is a sulfonic acid type-macroporous strong acid ion exchange resin whose Hammett index of acid strength is $H_0 < -10$, and a H$^+$ exchange capacity of ion exchange resin is greater than 1.0 mmol/L; and
the molecular sieve is selected from at least one of HY, Hβ and HZSM-5 molecular sieves with topological structures of FAU, BEA, and MFI; and as measured by NH$_3$ chemisorption determination, the molecular sieve has a weak acid site density ranging from 0.005 mmol/g to 0.35 mmol/g, a medium-strength acid site density ranging from 0.01 mmol/g to 0.5 mmol/g, and a strong acid site density ranging from 0.003 mmol/g to 0.15 mmol/g.
2. The method for producing dicarboxylic acid of claim 1, wherein the cyclic olefin comprises five or more carbon atoms and a carbon-carbon double bond structure.
3. The method for producing dicarboxylic acid of claim 1, wherein the cyclic olefin is selected from at least one of a compound with a chemical formula represented by formula I, a compound with a chemical formula represented by formula II, a compound with a chemical formula represented by formula III, and a compound with a chemical formula represented by formula IV:

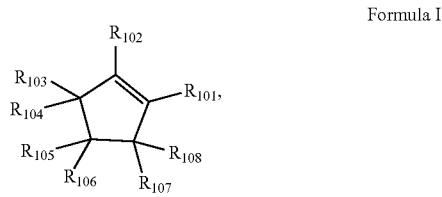

Formula I

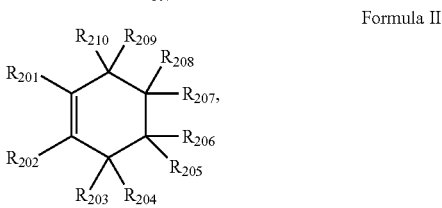

Formula II

-continued

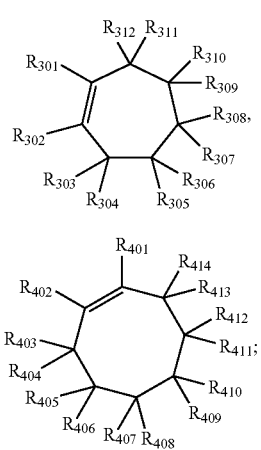

Formula III

Formula IV wherein, $R_{101}$, $R_{102}$, $R_{103}$, $R_{104}$, $R_{105}$, $R_{106}$, $R_{107}$, and $R_{108}$ in formula I are independently selected from H, $C_1$ to $C_3$ hydrocarbon group, halogen element or $C_1$ to $C_3$ halogenated hydrocarbon group;

wherein, $R_{201}$, $R_{202}$, $R_{203}$, $R_{204}$, $R_{205}$, $R_{206}$, $R_{207}$, $R_{208}$, $R_{209}$ and $R_{210}$ in formula II are independently selected from H, $C_1$ to $C_3$ hydrocarbon group, halogen element or $C_1$ to $C_3$ halogenated hydrocarbon group;

wherein, $R_{301}$, $R_{302}$, $R_{303}$, $R_{304}$, $R_{305}$, $R_{306}$, $R_{307}$, $R_{308}$, $R_{309}$, $R_{310}$, $R_{311}$, and $R_{312}$ in formula III are independently selected from H, $C_1$ to $C_3$ hydrocarbon group, halogen element or $C_1$ to $C_3$ halogenated hydrocarbon group; and $R_{401}$, $R_{402}$, $R_{403}$, $R_{404}$, $R_{405}$, $R_{406}$, $R_{407}$, $R_{408}$, $R_{409}$, $R_{410}$, $R_{411}$, $R_{412}$, $R_{413}$, and $R_{414}$ in formula IV are independently selected from H, $C_1$ to $C_3$ hydrocarbon group, halogen element or $C_1$ to $C_3$ halogenated hydrocarbon group.

4. The method for producing dicarboxylic acid of claim 1, wherein a molar ratio of the lower monocarboxylic acid to the cyclic olefin is in a range from 0.2 to 10.0, and a space velocity of the cyclic olefin is in a range from 0.6 to 3.0 $g \cdot g^{-1} \cdot h^{-1}$.

5. The method for producing dicarboxylic acid of claim 1, wherein the addition reaction is carried out in one or more reactors; and the reactor is selected from at least one of a fixed bed reactor and a kettle-type reactor.

6. The method for producing dicarboxylic acid of claim 1, wherein the addition reaction is carried out under a pressure ranging from 0.1 to 2.0 MPa, and a reaction temperature ranging from 50 to 150° C.

7. The method for producing dicarboxylic acid of claim 1, wherein the oxidation reaction in step 2) is carried out at a reaction temperature ranging from 40 to 120° C., and a reaction pressure ranging from 0.1 to 0.5 MPa.

8. The method for producing dicarboxylic acid of claim 1, wherein the oxidant in step 2) is selected from at least one of $HNO_3$, nitrite, and hydrogen peroxide.

9. The method for producing dicarboxylic acid of claim 1, wherein the oxidation catalyst in step 2) is selected from at least one of $NH_4VO_3$, $Cu(NO_3)_2$, $Co(NO_3)_2$, $Fe(NO_3)_3$, ammonium molybdate, ammonium tungstate, and heteropoly acid.

10. The method for producing dicarboxylic acid of claim 1, wherein a molar ratio of the oxidant to the cyclic carboxylic acid ester in step 2) is
oxidant: cyclic carboxylic acid ester=3:1 to 15:1; and
an amount of the oxidation catalyst satisfies that: after the oxidation catalyst is added, a mass concentration of each oxidation catalyst in the oxidation reaction system ranges from 0.01% to 1.0%.

11. The method for producing dicarboxylic acid of claim 1, wherein the intermediate product system comprising the cyclic carboxylic acid ester is a mixed system after the addition reaction is completed or only refers to the cyclic carboxylic acid ester.

12. The method for producing dicarboxylic acid of claim 1, further comprising step 3): after the ring-opening oxidation reaction is completed, separating the lower monocarboxylic acid in the obtained product and recycling the same to the raw material of the addition reaction in step 1.

* * * * *